United States Patent
Kumar et al.

(10) Patent No.: US 7,670,384 B2
(45) Date of Patent: Mar. 2, 2010

(54) BONE GRAFT COMPOSITION COMPRISING A BONE MATERIAL AND A CARRIER COMPRISING DENATURED DEMINERALIZED BONE

(75) Inventors: Mukesh Kumar, Warsaw, IN (US); Ned M. Hamman, Leesburg, IN (US); Michael D. Leach, Warsaw, IN (US); John Manocchio, Paramus, NJ (US); Paul D'Antonio, Morristown, NJ (US); Daryl L. Carter, Hopatcong, NJ (US)

(73) Assignee: Biomet Manufacturing Corp., Warsaw, IN (US)

( * ) Notice: Subject to any disclaimer, the term of this patent is extended or adjusted under 35 U.S.C. 154(b) by 219 days.

(21) Appl. No.: 11/407,409

(22) Filed: Apr. 19, 2006

(65) Prior Publication Data

US 2006/0280803 A1 Dec. 14, 2006

Related U.S. Application Data

(63) Continuation-in-part of application No. 10/964,950, filed on Oct. 14, 2004, now abandoned.

(51) Int. Cl.
*A61F 2/28* (2006.01)
*A61K 35/32* (2006.01)
(52) U.S. Cl. .............. 623/23.63; 623/23.51; 623/23.56; 424/549
(58) Field of Classification Search .............. 623/23.63, 623/23.51, 23.56; 424/549
See application file for complete search history.

(56) References Cited

U.S. PATENT DOCUMENTS 1,456,469 A    5/1923  Schwidetzky
2,541,621 A    2/1951  Thompson
4,172,128 A  * 10/1979  Thiele et al. ................ 424/549
4,191,747 A    3/1980  Scheicher
4,200,478 A    4/1980  Jacino et al.

(Continued)

FOREIGN PATENT DOCUMENTS

WO    WO 97/25941     7/1997
WO    WO 00/45870     8/2000
WO    WO 00/54821     9/2000

OTHER PUBLICATIONS

Symphony™ Graft Delivery System: Bronze, Medical & Scientific Equipment, Industrial Designers Society of America, Tanaka Kapec Design Group, Inc. and DePuy AcroMed Inc.; Idea 2002 Showcase: Medical and Scientific Equipment, available at http://new.idsa.org/idea/idea2002/B9609.htm.
Symphony™ Graft Delivery System: Surgical Technique, DePuy AcroMed, Inc., 2001.
Mylar® Polyester Film: Introduction to Mylar® Polyester Films, DuPont Teijin Films, 2003.

*Primary Examiner*—Karen Cochrane Carlson
*Assistant Examiner*—Rosanne Kosson
(74) *Attorney, Agent, or Firm*—Harness, Dickey & Pierce, P.L.C.

(57) ABSTRACT

Formed compositions for application to a bone surface of a human or animal subject, comprising: a bone material; and a carrier comprising denatured demineralized bone, where the composition is formed into a shape suitable for administration to the bone. Methods are provided for making formed compositions for application to a bone surface of a human or animal subject comprise mixing a demineralized bone and water; heating the mixture to form a carrier; mixing the carrier with bone to form a moldable composition; and molding the moldable composition to produce a formed composition. Several apparatuses are provided in which to hydrate the formed bone composition. Methods of hydrating a formed bone composition are also provided.

45 Claims, 8 Drawing Sheets

U.S. PATENT DOCUMENTS

| | | |
|---|---|---|
| 4,277,184 A | 7/1981 | Solomon |
| 4,394,370 A | 7/1983 | Jefferies |
| 4,698,055 A | 10/1987 | Sealfon |
| 4,789,663 A | 12/1988 | Wallace et al. |
| 4,958,622 A | 9/1990 | Selenke |
| 5,073,373 A | 12/1991 | O'Leary et al. |
| 5,236,456 A | 8/1993 | O'Leary et al. |
| 5,263,991 A | 11/1993 | Wiley et al. |
| 5,290,558 A | 3/1994 | O'Leary et al. |
| 5,314,476 A | 5/1994 | Prewett et al. |
| 5,356,629 A | 10/1994 | Sander et al. |
| 5,405,390 A | 4/1995 | O'Leary et al. |
| 5,507,813 A | 4/1996 | Dowd et al. |
| 5,531,791 A | 7/1996 | Wolfinbarger, Jr. |
| 5,562,616 A | 10/1996 | Haber et al. |
| 5,697,903 A | 12/1997 | Fischer |
| 5,697,932 A | 12/1997 | Smith et al. |
| 5,824,084 A | 10/1998 | Muschler |
| 5,842,786 A | 12/1998 | Solomon |
| 5,908,054 A | 6/1999 | Safabash et al. |
| 5,957,166 A | 9/1999 | Safabash |
| 6,019,765 A | 2/2000 | Thornhill et al. |
| 6,030,635 A | 2/2000 | Gertzman et al. |
| 6,045,555 A | 4/2000 | Smith et al. |
| 6,049,026 A | 4/2000 | Muschler |
| 6,062,722 A | 5/2000 | Lake |
| 6,142,998 A | 11/2000 | Smith et al. |
| 6,180,605 B1 | 1/2001 | Chen et al. |
| 6,180,606 B1 | 1/2001 | Chen et al. |
| 6,294,187 B1 | 9/2001 | Boyce et al. |
| 6,309,395 B1 | 10/2001 | Smith et al. |
| 6,326,018 B1 | 12/2001 | Gertzman et al. |
| 6,395,017 B1 | 5/2002 | Dwyer et al. |
| 6,437,018 B1 | 8/2002 | Gertzman et al. |
| 6,458,375 B1 | 10/2002 | Gertzman et al. |
| 6,576,249 B1 | 6/2003 | Gendler et al. |
| 6,648,133 B1 | 11/2003 | Blaschke et al. |
| 6,696,073 B2 | 2/2004 | Boyce et al. |
| 6,723,131 B2 | 4/2004 | Muschler |
| RE38,522 E | 5/2004 | Gertzman et al. |
| 7,077,339 B2 | 7/2006 | Leach |
| 2001/0018614 A1 | 8/2001 | Bianchi |
| 2002/0018796 A1 | 2/2002 | Wironen |
| 2002/0076429 A1 | 6/2002 | Wironen et al. |
| 2002/0082694 A1 | 6/2002 | McKay |
| 2002/0098222 A1 | 7/2002 | Wironen et al. |
| 2003/0009235 A1 | 1/2003 | Manrique et al. |
| 2003/0044445 A1 | 3/2003 | Kay et al. |
| 2004/0153090 A1 | 8/2004 | Vandewalle |
| 2004/0167617 A1 | 8/2004 | Voellmicke et al. |

* cited by examiner

BONE GRAFT COMPOSITION COMPRISING A BONE MATERIAL AND A CARRIER COMPRISING DENATURED DEMINERALIZED BONE

CROSS-REFERENCE TO RELATED APPLICATIONS

This application is a continuation-in-part application of U.S. application Ser. No. 10/964,950, filed on Oct. 14, 2004, now abandoned, the disclosure of which is incorporated herein by reference.

INTRODUCTION

The present teachings relate to a bone repairing composition, methods of production and use thereof and related hydration apparatus. In particular, the teachings relate to formed compositions useful in repairing osseous defects which can be inserted into the defect without preparation or manipulation.

A bone repairing composition or filler can be used to correct defects caused by trauma, pathological disease, surgical intervention, or other situations where defects need to be managed in osseous surgery. Because defects are usually jagged or irregularly shaped, it can be important to have the bone filler of an appropriate composition to facilitate placement of the filler into the surgical site. The surgeon can trowel the filler into the injury site and use his or her fingers and/or suitable instruments to shape it into the proper configuration.

Bone reconstruction can be performed with various pastes, gels, or putty-like materials containing a natural collagen or human cadaveric donor bone base. Preferably, compositions are prepared from demineralized allograft bone matrix (DBM) that is taken from cadavers. The sterile DBM is available in cubes, shavings, or powder and is freeze-dried. Because the DBM is dry and difficult to manipulate, it can be made flowable or malleable with the addition of a wetting agent. The patient's blood has been used to mix the bone, bone powder, or collagen because blood offers the benefits of being available at the operative site, is non-immunogenic to the patient and contains proteins, monosaccharides, polysaccharides, and glucuronic acid which increase the healing process and regeneration of bone. Other wetting agents include monosaccharides, disaccharides, water dispersible oligosaccharides, polysaccharides, low weight organic solvents, including glycerol, polyhydroxy compounds, such as mucopolysaccharide or polyuronic acid, and various aqueous solutions. (See, e.g., U.S. Pat. No. 5,290,558, O'Leary et al., issued Mar. 1, 1994; U.S. Pat. No. 5,073,373, O'Leary et al., issued Dec. 17, 1991; U.S. Pat. No. 5,314,476, Prewett, et al., issued May 27, 1994; U.S. Pat. No. 5,507,813, Dowd, et al., issued Apr. 16, 1996; U.S. Pat. No. 4,191,747, Scheicher, issued Mar. 4, 1980; and U.S. Pat. No. 4,172,128, Thiele, et al., issued Oct. 23, 1979.) Compounds like GRAFTON® (Available from Osteotech, Inc., Eatontown, N.J., USA), a glycerol based, non-cross linkable composition and collagen suspended in various inert polyhydroxy compounds, are also used to make the demineralized bone malleable. Regardless of the exact components, a primary goal in bone reconstruction is that the filler be highly effective in inducing bone formation, become an integrated fixture at the application site and not become dislodged.

Many compositions known in the art are difficult to handle and shape. The malleable filler must be molded by the surgeon to fit into the proper configuration of the defect site. Even when the surgeon uses great care to mix the paste or gel and sculpt a form, there may be a risk that the implant will become dislodged and carried away by body fluids. Subsequently, these compositions may not be suitable for large defects.

It would be advantageous to provide a bone repairing composition that is non-immunogenic, osteogenic, is easily placed into injury sites, adheres to the injury sites, and is not easily displaced by bodily or other fluids. It would also be advantageous for the bone repairing composition to be ready to use in preformed shapes or universally sized patches or sheets, thus eliminating the need for significant sculpting and manipulation of the composition in the operating room. It would also be advantageous to provide a system to efficiently hydrate the compositions.

SUMMARY

The present teachings provide formed compositions for application to a bone surface of a human or animal subject, comprising:
(a) a bone material; and
(b) a carrier comprising denatured demineralized bone;
where the composition is formed into a shape suitable for administration to the bone.

Various methods are also provided for making formed compositions for application to a bone surface of a human or animal subject, comprising:
(a) mixing a demineralized bone and water;
(b) heating the mixture of demineralized bone and water to form a carrier;
(c) mixing the carrier with a bone material to form a moldable composition; and
(d) molding the moldable composition to produce a formed composition having a shape suitable for administration to the bone.

The teachings also provide methods of augmenting bone at a site in need thereof in a human or animal subject, comprising:
(a) adding water to a dried composition, comprising:
(i) a bone material; and
(ii) a carrier comprising denatured demineralized bone;
where the composition is formed into a shape suitable for administration to the bone; and
(b) applying the composition to the site.

The teachings also provide methods of augmenting a bone defect at a defect site having a specific shape in a human or animal subject, comprising:
(a) adding water to a dried composition comprising:
(i) a bone material; and
(ii) a carrier comprising denatured demineralized bone;
where the composition is formed into a site-specific shape having a mated shape to the specific shape of the bone defect; and
(b) applying the site-specific shaped composition to the defect site.

The teachings also provide hydration apparatuses which comprise:
(a) a retaining tube having a distal and proximal end, comprising:
(i) a removable plunger adapted for insertion into the retaining tube proximal, where the plunger includes a base;
(ii) a cap at the retaining tube distal end;
(iii) a side port having a valve, where the side port is located towards the distal end of the retaining tube; and
(iv) a chamber defined by a space between the plunger base and the cap; and (b) a hydrating tube having a distal end and a proximal end, comprising:
(i) a connector for attachment to the valve located at the hydrating tube distal end; and
(ii) a substantially closed cover at the hydrating tube proximal end.

The teachings also provide hydration apparatuses for a formed bone composition, comprising:
(a) a sleeve, comprising:
(i) a port having a valve; and
(ii) a lid;
where the sleeve dimensions substantially conform to the dimensions of the formed bone composition contained therein.

The present teachings also provide kits, comprising:
(a) an apparatus for hydrating formed bone compositions; and
(b) a hydration media.

The present teachings also provide methods of hydrating a formed bone composition, comprising:
(a) providing a dehydrated formed bone composition under a vacuum in a container comprising a port;
(b) connecting a hydrating tube containing a fluid and a fixed amount of vacuum space to the port; and
(c) drawing the fluid through the port and into the retaining tube to hydrate the formed bone composition.

The compositions and methods of the teachings provide benefits over methods, compositions and apparatus among those known in the art. Such benefits can include one or more of affording a graft material that is not easily dislodged from the site to which it is implanted, even in the presence of body fluids and after the passage of time, enhanced strength, and resistance to dissolution by blood or other fluids and easy hydration. Further areas of applicability will become apparent from the detailed description provided hereinafter. It should be understood that the Detailed Description and specific examples, while indicating preferred embodiments of the teachings, are intended for purposes of illustration only and are not intended to limit the scope of the teachings.

BRIEF DESCRIPTION OF THE DRAWINGS

The present teachings will become more fully understood from the detailed description and the accompanying drawings, wherein.

Figure 1:
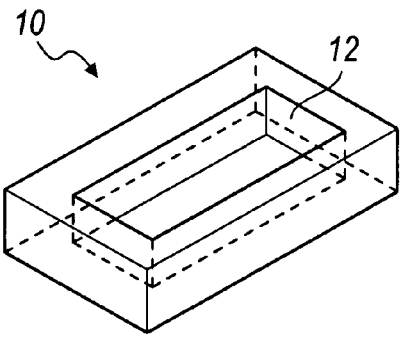
FIG. 1 depicts a formed bone composition according to various embodiments.
Figure 2:
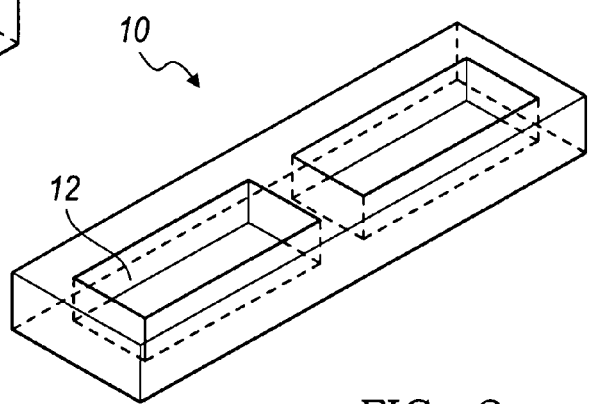
FIG. 2 depicts a formed bone composition having multiple channels according to various embodiments.

It should be noted that the figures set forth herein are intended to exemplify the general characteristics of apparatus, materials and methods among those of the teachings, for the purpose of the description of such embodiments herein. These figures may not precisely reflect the characteristics of any given embodiment, and are not necessarily intended to define or limit specific embodiments within the scope of the present teachings.

DETAILED DESCRIPTION

The compositions of the present teachings comprise a bone material and a carrier component. The following definitions and non-limiting guidelines must be considered in reviewing the description of the teachings set forth herein.

The headings (such as "Introduction" and "Summary") and sub-headings (such as "Methods of Augmenting a Bone Site" or "Hydration Apparatus") used herein are intended only for general organization of topics within the disclosure of the teachings, and are not intended to limit the disclosure of the teachings or any aspect thereof. In particular, subject matter disclosed in the "Introduction" may include aspects of technology within the scope of the teachings, and may not constitute a recitation of prior art. Subject matter disclosed in the "Summary" is not an exhaustive or complete disclosure of the entire scope of the teachings or any embodiments thereof. Classification or discussion of a material within a section of this specification as having a particular utility (e.g., as being a "carrier" or a "bone building" ingredient) is made for convenience, and no inference should be drawn that the material must necessarily or solely function in accordance with its classification herein when it is used in any given composition.

The citation of references herein does not constitute an admission that those references are prior art or have any relevance to the patentability of the teachings disclosed herein. Any discussion of the content of references cited in the Introduction is intended merely to provide a general summary of assertions made by the authors of the references, and does not constitute an admission as to the accuracy of the content of such references. All references cited in the Description section of this specification are hereby incorporated by reference in their entirety.

The Detailed Description and specific examples, while indicating embodiments of the teachings, are intended for purposes of illustration only and are not intended to limit the scope of the teachings. Moreover, recitation of multiple embodiments having stated features is not intended to exclude other embodiments having additional features, or other embodiments incorporating different combinations the stated of features. Specific examples are provided for illustrative purposes of how to make and use the compositions and methods of the teachings and, unless explicitly stated otherwise, are not intended to be a representation that given embodiments of the teachings have, or have not, been made or tested.

As used herein, the words "preferred" and "preferably" refer to embodiments of the teachings that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the teachings. As referred to herein, all compositional percentages are by weight of the total composition, unless otherwise specified.

As used herein, the word "include," and its variants, is intended to be non-limiting, such that recitation of items in a list is not to the exclusion of other like items that may also be useful in the materials, compositions, devices, and methods of the teachings.

Materials

The present teachings provide a formed composition for application to a bone surface of a human or animal subject, comprising:

(a) a bone material; and
(b) a carrier comprising denatured demineralized bone;
where the composition is formed into a shape suitable for administration to the bone.

As referred to herein, a "formed" composition has a non-random shape, preferably of a size and dimension suitable for implantation to the site of a bone surface. Formed compositions can be of any of a variety of shapes, including cubes or other blocks, sheets, rods, rings, and discs. In various embodiments the shapes can be specifically formed for a desired end-use application, as a site-specific pre-form.

Bone used in embodiments of the teachings can be obtained from cortical, cancellous and/or corticocancellous bone. (See, e.g., U.S. Pat. No. 5,507,813, Dowd, et al., issued Apr. 16, 1996, incorporated by reference.) Preferably, the bone is autologous bone or donated from a single member of the same species as the patient to reduce or prevent an immunogenic response. However, bone from multiple donors can be used in the compositions.

The "bone material" component of the present teachings is selected from bone powder, bone chips, bone shavings, and mixtures thereof. In a preferred embodiment, the bone material is dried demineralized bone powder. Suitable drying techniques include freeze drying, vacuum drying, air drying, temperature flux drying, molecular sieve drying, and other appropriate techniques. Preferably, the bone material comprises freeze dried bone. As used herein, the term "freeze dried" or "lyophilization" and variants thereof, means the process of isolating a solid substance from solution by freezing the solution and evaporating the ice under a vacuum. The dried bone material has a final moisture level of about less than 6% as recommended by the American Association of Tissue Banks. As used herein, the term "demineralized" and variants thereof, means a loss or decrease of the mineral constituents or mineral salts of the individual tissues or bone relative to their natural state. Preferably, the demineralized bone has a calcium concentration of about 1%. The demineralized bone powder has a particle size of less than about 1500 microns, more preferably less than about 1000 microns and more preferably, less than about 850 microns. In another preferred embodiment, the demineralized bone material has a particle size less than about 710 microns.

In various embodiments, the bone material can additionally comprise bone chips. The bone chips can be natural or demineralized. The bone chips range from about 750 to about 2000 microns, preferably from about 750 to about 1500 microns.

The carrier component is comprised of demineralized bone and an aqueous solution. The carrier component particles sizes are less than about 1500 microns, more preferably less than about 1000 microns and more preferably, less than about 850 microns. In another preferred embodiment, the demineralized bone material has a particle size less than about 710 microns.

The carrier component comprises from about 0.2% to about 40% of demineralized denatured bone, by weight of the carrier, more preferably from about 0.5% to about 25% and more preferably, from about 10% to about 20%. An aqueous solution such as water or saline makes up the remainder of the carrier component.

In various embodiments, autoclaving the carrier component results in the bone and water or saline mixture forming a gel or having a gel like consistency. As used herein, "autoclaving," and its variants, refers to a thermal procedure, such as that used for sterilization, where the solution is placed in a sealed chamber and subjected to high temperature and pressure. Specific autoclaving methods among those useful herein are further described in the methods section below. Methods among those useful herein are also disclosed in U.S. Pat. No. 6,576,249, Gendler et al., issued Jun. 10, 2003, incorporated by reference herein.

In various embodiments, the formed product comprises from about 10% to about 40% bone material, preferably from about 20% to about 30%. The carrier component comprises from about 60% to about 90%, preferably from about 70% to about 80% of the formed composition.

The relative percentages of the bone material and carrier component may vary based on the amounts of each component used and the addition of other materials such as bone building materials. As used herein, a "bone building material" is a compound that stimulates the growth of bone to replace the bone repairing composition. "Bone building material" includes calcium containing materials, nutrient factors, bone morphogenic proteins, growth factors, antibiotics, antimicrobials, anti-inflammatory agents, blood products, and mixtures thereof. (See, e.g., U.S. Pat. No. 6,180,606, Chen, et al., issued Jan. 30, 2001, incorporated by reference.) Depending on the bone building material or materials selected, the composition is osteogenic and osteoinductive. The bone building materials can be contained in or coated onto the surface of the composition.

"Calcium containing" materials include hydroxyapatite, monobasic, dibasic and tribasic calcium phosphates, calcium aluminates, calcium containing ceramics, porous calcium containing ceramic particles, and amorphous calcium phosphate.

As used herein, a "nutrient factor" is a compound or series of compounds used to sustain metabolic activities or used to promote normal physiologic function or optimal health. Nutrient factors include vitamins, hormones, individual or combinations of amino acids, carbohydrates or derivatives thereof, fats or derivatives thereof, alcohols or derivatives thereof, inorganic salts, and trace elements.

As used herein, a "Bone Morphogenic Protein" is any of the zinc metalloendopeptidase enzymes that are involved in induction of bone and cartilage formation. Bone Morphgenic Proteins include Bone Morphogenic Protein-2 (BMP-2), Bone Morphogenic Protein-2a (BMP-2a), Bone Morphogenic Protein-4(BMP-4), Bone Morphogenic Protein-5 (BMP-5), Bone Morphogenic Protein-6(BMP-6), Bone Morphogenic Protein-7(BMP-7), and Bone Morphogenic Protein-8(BMP-8).

As used herein, a "growth factor" is a substance that is operable to increase the size of a living being or any of its parts or to stimulate cell growth. Growth factors include Transforming Growth Factor-beta (TGF-β), Transforming Growth Factor-alpha (TGF-∝), Epidermal Growth Factor (EGF), Insulin-like Growth Factor-I or II, Interleukin-I, Interferon, Tumor Necrosis Factor, Fibroblast Growth Factor (FGF), Platelet Derived Growth Factor (PDGF), and Nerve Growth Factor (NGF).

As used herein, "antibiotics" include the chemicals produced by one organism that are effective to inhibit the growth of another organism and include semi-synthetics, and synthetics thereof. As used herein, agents that reduce, inhibit, or prevent the growth or transmission of foreign organisms in a patient means that the growth or transmission of a foreign organism is reduced, inhibited, or prevented in a statistically significant manner in at least one clinical outcome, or by any measure routinely used by persons of ordinary skill in the art as a diagnostic criterion in determining the same. Antibiotics can be selected from macrolides and lincosamines, quinolones and fluoroquinolones, carbepenems, monobactams, aminoglycosides, glycopeptides, tetracyclines, sulfonamides, rifampins, oxazolidonones, and streptogramins, synthetic moieties thereof, and combinations thereof. Example macrolides and lincosamines include azithromycin, clarithromycin, clindamycin, dirithromycin, erythromycin, lincomycin, and troleandomycin. Example quinolones and fluoroquinolones include cinoxacin, ciprofloxacin, enoxacin, gatifloxacin, grepafloxacin, levofloxacin, lomefloxacin, moxifloxacin, nalidixic acid, norfloxacin, ofloxacin, sparfloxacin, trovafloxacin, oxolinic acid, gemifloxacin, and perfloxacin. Example carbepenems include imipenem-cilastatin and meropenem. Example monobactams include aztreonam. Example aminoglycosides include amikacin, gentamicin, kanamycin, neomycin, netilmicin, streptomycin, tobramycin, and paromomycin. Example glycopeptides include teicoplanin and vancomycin. Example tetracyclines include demeclocycline, doxycycline, methacycline, minocycline, oxytetracycline, tetracycline, and chlotetracycline. Example sulfonamides include mafenide, silver sulfadizine, sulfacetamide, sulfadiazine, sulfamethoxazole, sulfasalazine, sulfisoxazole, trimethoprim-sulfamethoxazole, and sulfamethizole. An example oxazolidonone is linezolid. An example streptogramin is quinopristin+dalfopristin. Other suitable antibiotics include bacitracin, chloramphenicol, colistemetate, fosfomycin, isoniazid, methenamine, metronidazol, mupirocin, nitrofurantoin, nitrofurazone, novobiocin, polymyxin B, spectinomycin, trimethoprim, coliistin, cycloserine, capreomycin, ethionamide, pyrazinamide, para-aminosalicyclic acid, and erythromycin ethylsuccinate+sulfisoxazole. Still further antibiotics may also include the ample spectrum penicillins, penicillins and beta lactamase inhibitors, and cephalosporins. The antibiotics may be used alone or in combination.

As used herein, an "anti-inflammatory" is an agent that reduces inflammation without directly antagonizing the causative agent. "Anti-inflammatories" include steroidal and non-steroidal anti-inflammatory agents.

As used herein, a "blood product" is a product, any component of which is derived from blood. Blood products include whole blood and blood fractions, such as plasma, blood cells, blood factors, blood related proteins, unspecialized cells such as stem cells (including adipose derived stem cells), or specialized cells, e.g., types of leukocytes such as lymphocytes and dendritic cells.

Other suitable materials can include inorganic materials, metals, such as mesh titanium or titanium alloy, amino acids, gelatin, collagen, naturally occurring or synthetic therapeutic drugs, proteins, and enzymes.

The bone repairing composition is formed into a shape. As used herein, "formed" refers to a rigid object having fixed dimensions and specific volume due to the cohesion of its components. The formed shape can be a block, disc, patch, ring, cylinder, or be site-specific preformed to fit the injury site.

Methods of Preparation and Use of Formed Bone Composition

The present teachings provide methods of making a formed composition and methods of augmenting bone at a site in need of augmentation. Such methods include those for making a formed composition for application to a bone surface of a human or animal subject, the methods comprising:
(a) mixing a demineralized bone and water;
(b) heating the mixture of demineralized bone and water to form a carrier;
(c) mixing the carrier with a bone material to form a moldable composition;
(d) molding the moldable composition to produce a formed composition having a shape suitable for administration to the bone.

Preparing a Formed Composition

Preparing the Bone

Bone is collected from a donor source and can include the entire bone or bone fragments from cancellous or cortical bone. In a preferred embodiment, the subject is of the same species as the donor. For example, all of the bone used to prepare a composition for a human patient can be sourced from a single human cadaveric donor. Any adherent tissues can be removed from the bone by standard bone cleaning protocol.

In various embodiments, the bone is milled into particles ranging from about 700 microns to about 2000 microns. As used herein, the term "milled" and conjugations thereof, refers to shaping a tissue to the desired size by crushing, chopping, cutting, shaving, grinding, or pulverizing. In embodiments where several sizes of bone are be used, it is understood that the milling process can be repeated and the respective bone portions can be reserved and assigned accordingly. Commercially available milling and sieving devices can be used or bone can be purchased in the form of an allograft matrix in the desired particle size or sizes.

Milled bone can be defatted by soaking or washing the bone in ethanol because the high polarity of ethanol solubizes the less polar lipids. A preferred ethanol solution is at least 60% ethanol, volume to volume, in deionized/distilled water. A more preferred ethanol solution is 100% ethanol. The ethanol bath also disinfects the bone by killing vegetative microorganisms and viruses. A further antiseptic step can include treatment of the milled bone with a hydrogen peroxide solution.

In embodiments containing natural bone chips, a portion of the milled bone can be set aside before demineralizing of the other components.

Preparing the Bone Material

To prepare the bone material, milled bone is demineralized using an acidification or chelating process. Acids used include inorganic acids such as hydrochloric acid or organic acids such as peracetic acid. Chelating agents include disodium ethylenediaminetetraacetic acid ($Na_2EDTA$).

The time required to demineralize the bone may vary depending on the concentration of acid or chelating agent used, the displacement or flow of the solution and the desired final concentration of calcium in the bone. For example, in an embodiment using hydrochloric acid, at an acid concentration of 0.1 to 2.0 N, the bones can be soaked in the acid bath for up to 24 hours. The calcium or mineral concentration in the milled bone can be monitored by measuring the pH of the acid solution using a calcium specific electrode or a standard pH meter. In a preferred embodiment, the acid wash or soak ceases when the calcium concentration of the bone is less than 1%.

After demineralization, the pH of the bone is adjusted by removing the acid with a deionized/distilled water wash until the pH of the bone approximates that of the water. It is not outside of the scope of embodiments of the teachings to expedite the neutralization of the bone using an ionic strength adjuster such as a biocompatible buffer solution.

Bone for the bone material can then be lyophilized to a moisture level of less than 6% using standard drying techniques including, but not limited to, freeze drying, vacuum drying and evaporation.

Preparing the Carrier Component

To prepare the carrier component, the milled bone is demineralized according to the procedure set forth above. The demineralized bone is then added to an aqueous component such as water or a saline solution. The demineralized bone can be in a wet, moist or dry state or a combination of states. Each 5 to 25 grams of demineralized bone requires the addition of about 100 grams of water or a saline solution. It is understood that adjustments can be made to these ratios depending on the bone size and bone state (chips, powder, fragments, etc.).

The carrier is then heat treated. Suitable heat treatments incorporate boiling, steaming, or the use of an oven. Preferably, the carrier is autoclaved at a temperature of from about 100° C. to about 150° C., at a pressure of from about 10 psi to about 20 psi, for a period of a about 0 minutes to 2 hours. In a preferred embodiment, the mix is autoclaved at 121° C. under a pressure of 15 psi for 60 minutes. The duration of autoclaving can be adjusted depending upon the amount of demineralized bone and the amount and type of liquid used.

Preparing the Moldable Material

The carrier component and bone material component are combined to form a paste or moldable material. This mixing can be achieved when the carrier component is mostly in the liquid state or when it has formed a gelatinous mass such as that achieved by cooling. The mixing can be performed in a separate container or it can be performed in the mold, as detailed later herein.

Embodiments of the teachings consist of about 100 grams of the carrier component mixed with about 25 to about 40 grams of the bone material component. In a preferred embodiment, about 100 grams of the carrier component is mixed with about 27 to 35 grams of the bone material component. Depending on the formulation used, the carrier component comprises from about 72% to about 80% of the paste weight and the bone material component comprises from about 20% to about 28% of the paste weight.

In various embodiments containing bone chips, the bone chips comprise about 10% of the bone material weight or about 2% of the total paste weight. For example, in preferred embodiments where 28 grams of the bone material component is used, 2.8 grams of natural bone chips are added to the paste. The bone chips can be added during or after mixing of the carrier component and bone material component. Bone building materials, such as those described herein, can also be added during or after the paste preparation step. The timing of addition is important because the bone building properties of the material can be compromised if the material is added before the demineralization step. For example, the bone enhancing qualities of supplemental calcium phosphate would be futile because it would wash away during the acidification or chelating process. Nonetheless, it is possible to add other biologically active agents in the formulation at this stage. These biological agents include, for example, antibiotics and growth factors.

Preparing the Formed Composition

This paste is then "cast" into the formed shape. As used herein, the term "cast" relates to the process of making impressions or of shaping in a mold. The casts can be formed by placing the moldable material into sterilized and optionally disposable molds. The paste can be delivered into the mold by spreading with a spatula type device or dispensing with a syringe, for example.

In various embodiments, the filled mold can be placed inside of a sterilized dual chamber package. Packaging is preferably durable, flexible, has barrier resistance to moisture, chemicals, grease, and bacteria, maintains its integrity upon exposure to low temperatures and is easy to handle in a medical or clinical setting. Suitable packaging materials can include thermoplastic films, polyester films, para-aramid fibers, polyethylene fibers, and combinations thereof. In a preferred embodiment, the inner packaging includes a polyester film, such as Mylar® and a polyethylene fiber, such as Tyvek® (both DuPont, Wilmington, Del., USA) and the outer compartment is a moisture resistant foil bag made of aluminum and transparent plastic with a Tyvek® Header pouch. Moisture can be drawn from the filled Tyvek Mylar® aluminum/plastic chamber by lyophilizing, vacuum drying, air drying, temperature flux drying, molecular sieve drying, and/or other suitable drying techniques. Preferably, moisture is removed by lyophilizing until the moisture content decreases to about 6% of the cast weight. In a preferred embodiment, the moisture level is less than 6%.

In an embodiment where the bone building material is loaded after the paste preparation step, the mold can be lined with the bone building material or biologically active ingredients which coat the outer surface of the composition. The mold can also incorporate structural features such as ridges, corrugation, or other surface indentations to impart structural stability and rigidity.

In various embodiments where the paste can be placed into a cast using a syringe, a system can be used which incorporates the mold and places it in communication with a syringe. Suitable devices are discussed later herein.

The formed composition can have a generic or site specific shape. Generic formed compositions include sheets, patches, rings, cubes, cylinders, or discs to be formed to an injury site during surgery. In embodiments where the formed shape is a patch or sheet, the rigidity of the composition can be altered. A sheet material which is more pliable or less pliable can be accomplished by changing the sheet thickness or adding ridges or corrugation, for example.

The formed composition can also be shaped for specific uses. As shown in FIGS. 1 through 4, the exemplary formed compositions 10 are trough-style and contain a channel 12 or multiple channels. The channels 12 can be used to store a bone building material 14. For example, the channel(s) 12 can be filed with autograft bone chips, bone graft substitute, or any other bone building material disclosed herein. The channel 12 is also useful for facilitating ingrowth of new bone.

Specific uses of the trough-style graft 10 include posterolateral fusions or high tibial osteotomy for example. The rounded trough-style formed composition 12 depicted in FIG. 4 can be advantageously used in spinal applications. Specific uses of the trough-style embodiments are detailed later herein.

A site specific formed composition can have the dimensions of the void to be filled and does not require additional manipulation in the operating room. The dimensions can be acquired using an x-ray of the site of the defect as a reference for size and shape. The x-ray can be scaled to the appropriate dimensions for the cast. Depending on the quantity and type of bone defect repairs required, a plurality of generic and site specific formed compositions can be used during the surgery.

Additionally, site specific formed compositions can conform to the geometry of the adjacent host bone to facilitate efficient incorporation of new bone.

Methods of Augmenting a Bone Site

Embodiments of the teachings can be used to repair bone defects. As used herein, "bone defects" or "injury sites", and variants thereof, refer to bone imperfections caused by birth defect, trauma, disease, decay, or surgical intervention, and the desired repair can be for cosmetic or therapeutic reasons.

Embodiments of the bone repairing composition can be used to correct bone defects in orthopedic, neurosurgical plastic, or reconstructive surgery, in periodontal procedures, and in endodontic procedures. Examples include repair of simple and compound fractures and non-unions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, tumor surgery, e.g. deficit filling, discectomy, laminectomy, excision of spinal cord tumors, anterial cervical and thoracic operations, repair of spinal injuries, scoliosis, lordosis and kyphosis treatments, intermaxillary fixation of fractures, mentoplasty, temporomandibular joint replacement, alveolar ridge augmentation and reconstruction, inlay bone grafts, implant placement and revision, sinus lifts, etc. The standard surgical and dental procedures are suitable for use with the various methods. (See, e.g., U.S. Pat. No. 6,180,606, Chen, et al., issued Jan. 30, 2001 and U.S. Pat. No. 5,507,813, Dowd, et al., issued Apr. 16, 1996.)

An aqueous solution, preferably containing water, is added to the dried bone repairing composition and the composition can be placed into the site or defect. In one embodiment, adding water to the dried bone can be achieved by adding blood to the composition. Hydration blood includes, but is not limited to, whole blood and blood components such as, red blood cells and components, white blood cells and components, plasma, plasma fractions, plasma serum, platelet concentrate, blood proteins, thrombin, and coagulation factors.

In embodiments where the formed composition is in sheet or patch form, the surgeon can simply place a single patch or several patches in the defect and shape it appropriately by hand or with a surgical tool. When the device is site specific preformed, the surgeon can match the contour of the composition with the contour of the injury and inserts the composition into the void. Any combination of site specific or generic patches can be used to fill a defect.

The formed composition can reconstitute or rehydrate while in the defect site. Ambient fluids such as blood are absorbed after a few minutes. Extra corpus fluids, including but not limited to, saline, water or a balanced salt solution (140 mm NaCl, 5.4 mm KCl, pH 7.6) are used to expedite the hydration. In an alternative embodiment, the formed bone composition can be reconstituted away from the defect site using the subject's blood or extra corpus fluids. As described later herein, various hydration apparatus can also be used to facilitate hydration of the formed composition before augmenting the bone site.

The composition can be made pliable to soften the device, allowing for easy manipulation and fit into the defect site. Suitable methods include application of heat or hydration by the direct application of warm aqueous based solutions to the formed composition. In various embodiments, a heating element can be used to transfer thermal energy to the formed composition. Suitable heating elements can use electrical, mechanical or chemical means to generate the thermal energy. For example, a heat pack can include a self-contained and user activated exothermic chemical means to generate heat and the pack can be disposed adjacent to or enclose a receptacle containing the formed composition. Upon initiating the exothermic reaction, heat is transferred through the heat pack and to the formed composition. Exemplary heating devices are disclosed in U.S. Pat. No. 5,263,991, Wiley, et al, issued Nov. 23, 1993, incorporated by reference. It is understood that the appropriate temperature and timing of the heat application depends on the dimensions, quantity and contents of the formed composition(s) and the selected heating techniques.

Hydration Apparatus and Kits

Hydration Apparatus

Various embodiments of the present teachings provide hydration apparatuses which comprise:

(a) a retaining tube having a distal and proximal end, comprising:
  (i) a removable plunger adapted for insertion into the retaining tube proximal end, where the plunger includes a base;
  (ii) a cap at the retaining tube distal end;
  (iii) a side port having a valve, where the side port is located towards the distal end of the retaining tube; and
  (iv) a chamber defined by a space between the plunger base and the cap, and (b) a hydrating tube having a distal end and a proximal end, comprising:
  (i) a connector for attachment to the valve located at the hydrating tube distal end; and
  (ii) a substantially closed cover at the hydrating tube proximal end.

Figure 5:
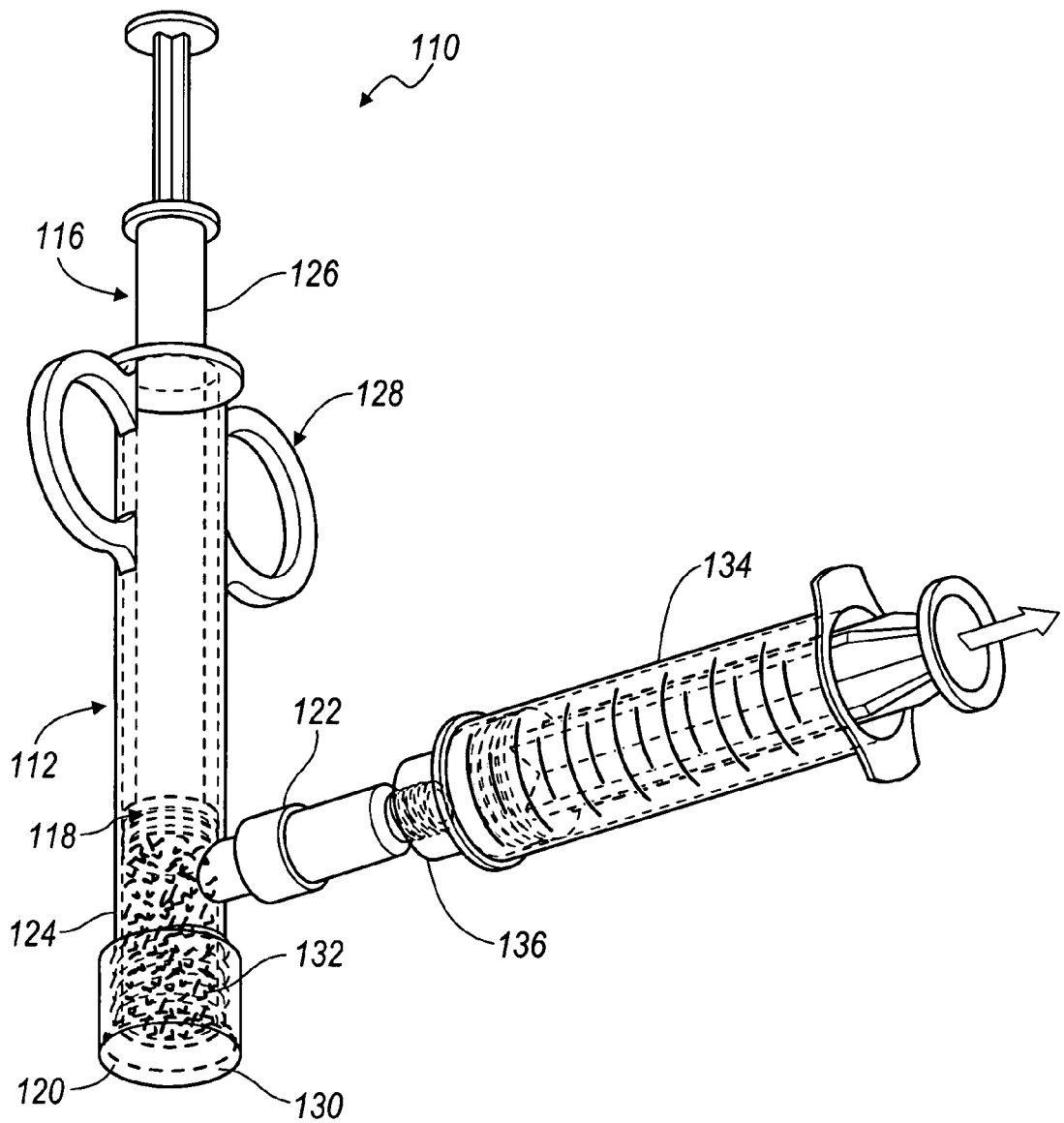
FIG. 5 depicts a side view of an apparatus according to various embodiments.
Figure 6:
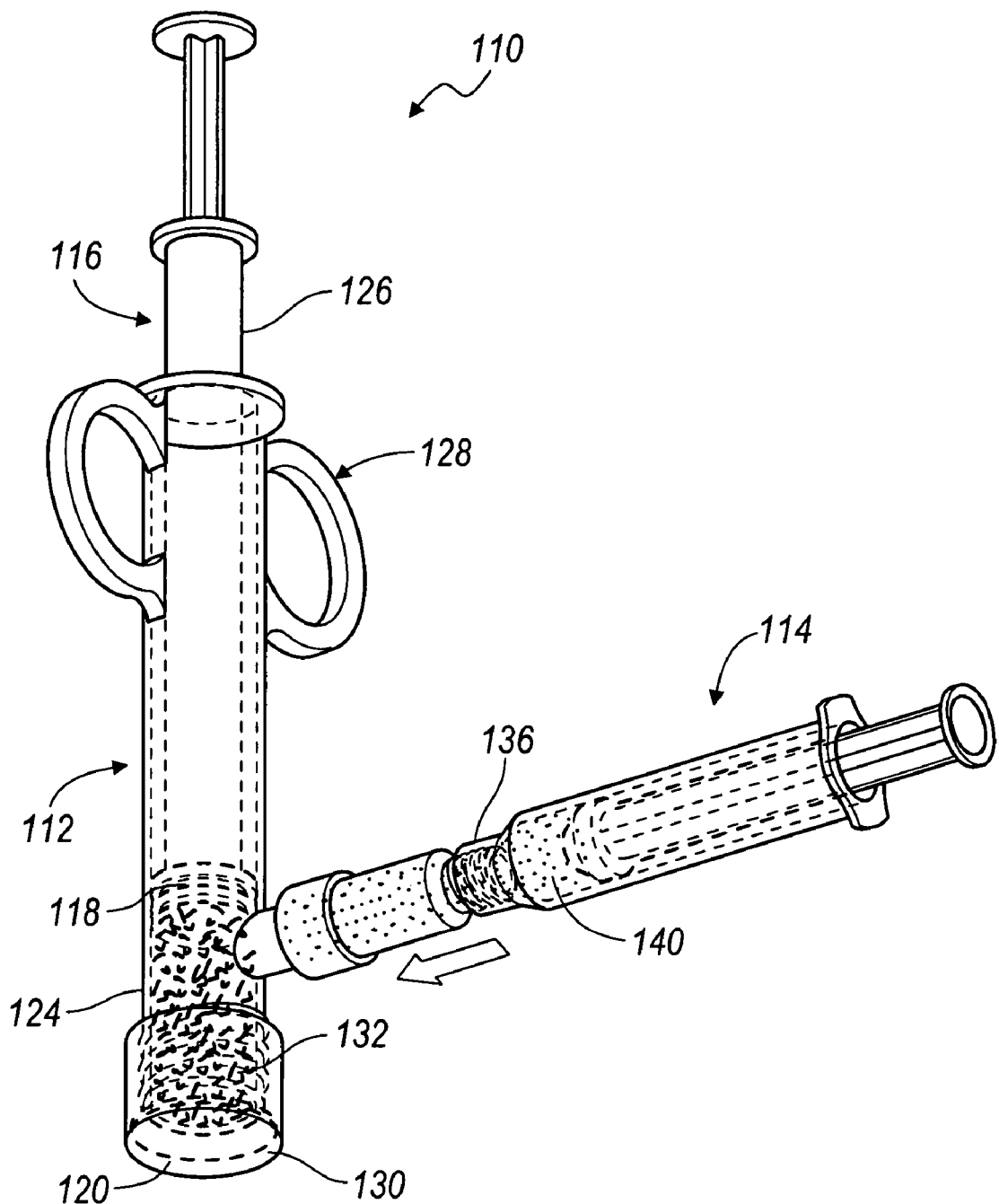
FIG. 6 depicts a side view of an apparatus according to various embodiments.
Figure 7:
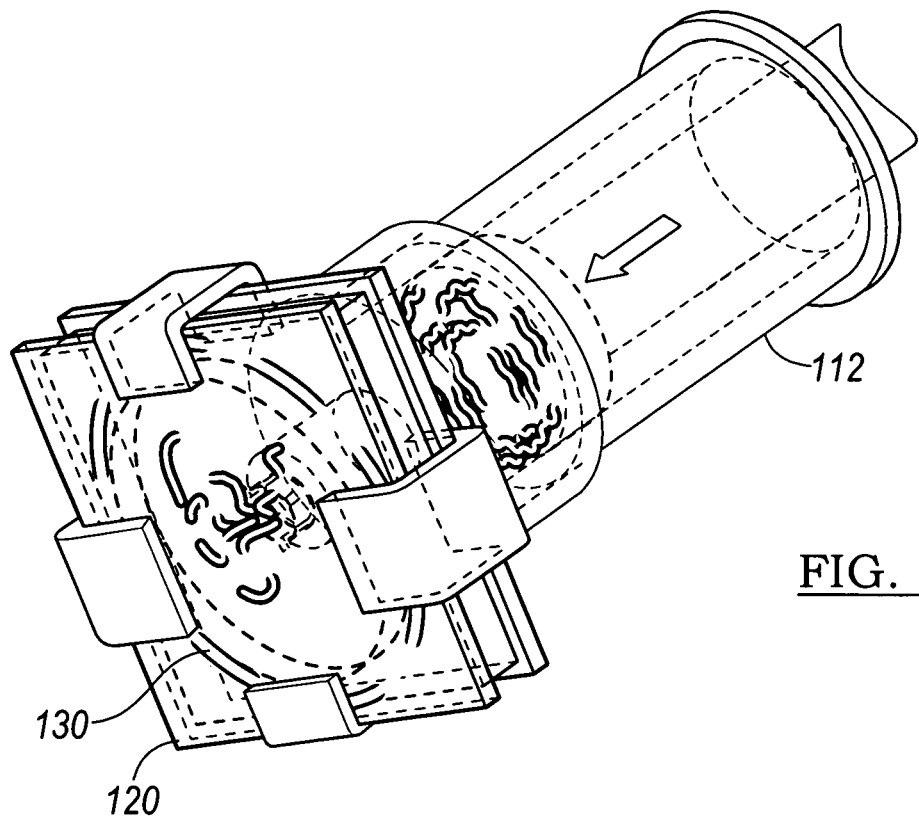
FIG. 7 depicts a partial view of a retaining tube and cap according to various embodiments.
Figure 8:
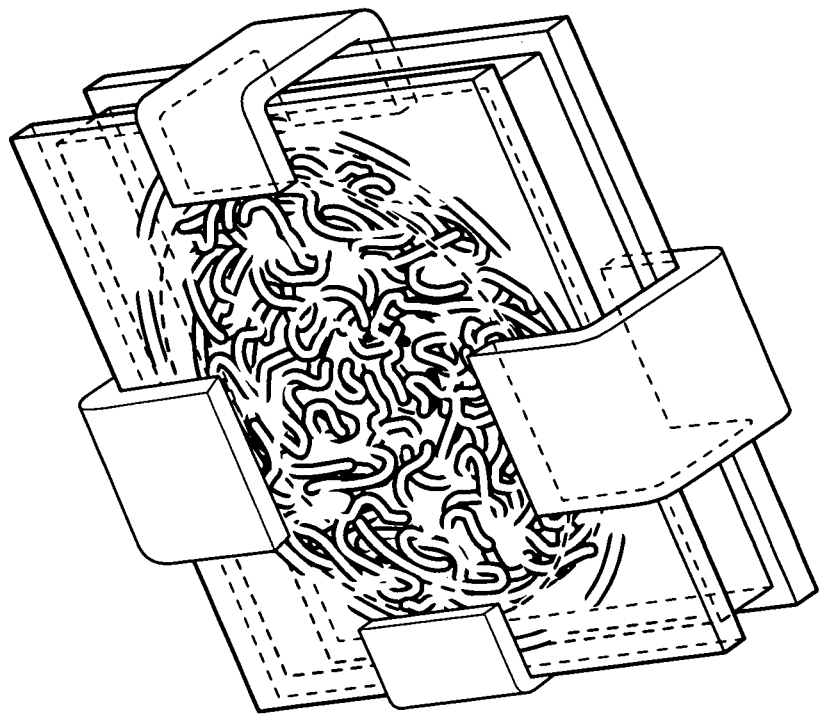
FIG. 8 depicts a view of a cap according to various embodiments.
Figure 9:
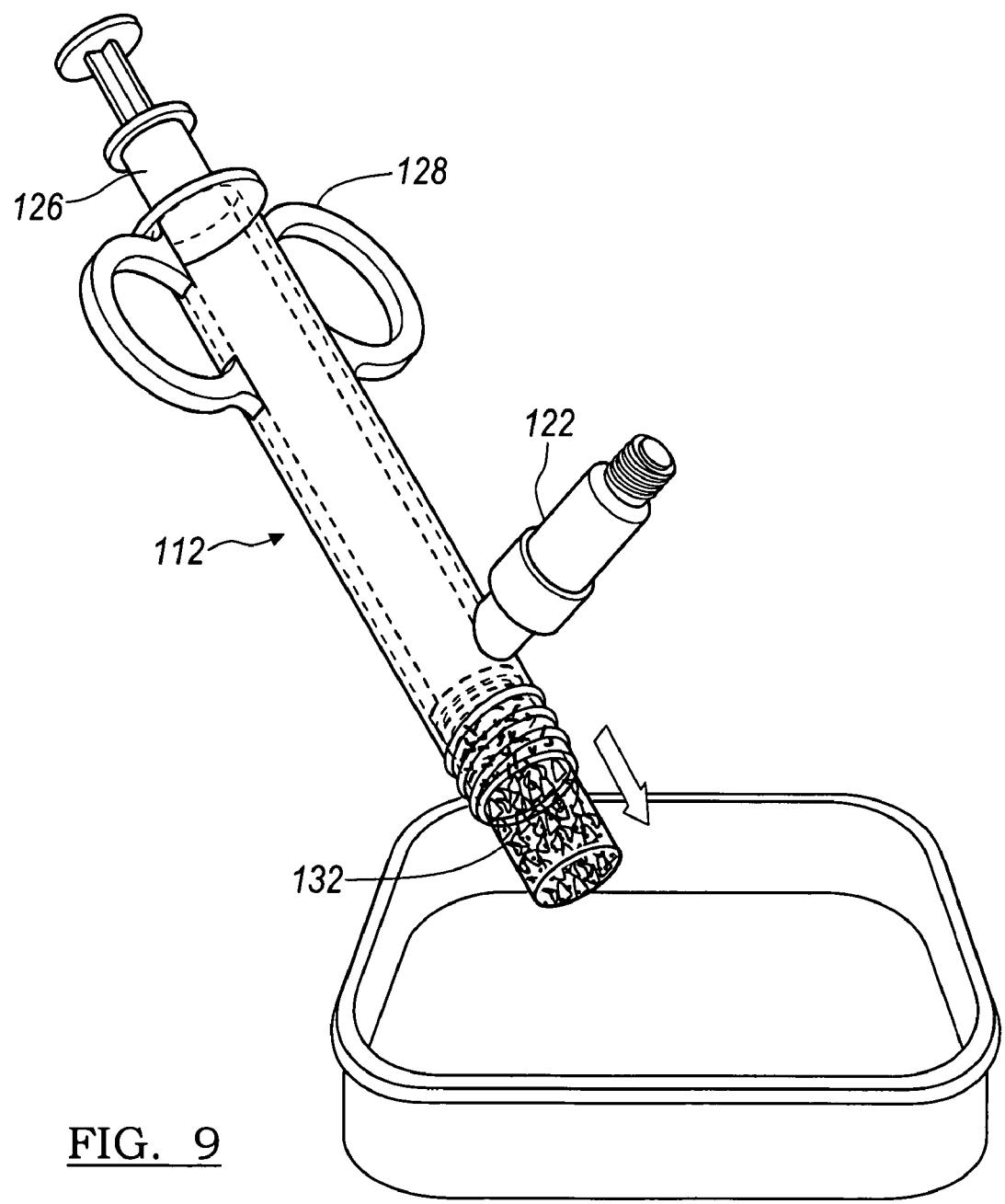
FIG. 9 depicts a method of using an apparatus according to various embodiments.

As depicted in FIGS. 5 and 6, an apparatus 110 of the present teachings can include a retaining tube 112 and a hydrating tube 114. As used herein, a "tube" can include any elongated hollow structure defined by a wall having at least one opening which allows for either the containment or passage of a material. While certain embodiments are depicted with the tube having a cylindrical shape, the tube can be of any other suitable shape. The tubes and related components of the present teachings can be made of any suitable material such as plastics, glass, or metals. The selection of materials or combinations thereof can be made in anticipation of material storage and conditions. For example, it may be desirable to use an expendable material in an embodiment where the apparatus 110 is disposable. In other embodiments, it may be desirable to use a durable biocompatible polymer when the apparatus 110 will store materials which can be implanted into a defect site, or store those materials for a long period of time or under particular temperature, humidity and/or pressure conditions.

The retaining tube 112 has a proximal end and a distal end and comprises a removable plunger 116 having a base 118, a cap 120, a side port 122 having a valve and a chamber 124. The removable plunger 116 comprising a rod 126 and a base 118 is located at the proximal end of the retaining tube 112. The size of plunger base 118 can be selected to fit within the retaining tube proximal end opening and pass through at least a segment of the retaining tube 112. The rod 126 can be operably attached to the plunger base 118 such that upon engaging the rod 126, the plunger base 118 passes through the retaining tube 112. The retaining tube 112 can also include a handle 128 or other suitable control means to facilitate movement of the rod 126 and base 118 through the retaining tube 112.

The cap 120 is located at the distal end of the retaining tube 112. The cap 120 can be of a sufficiently larger diameter than the distal end of the retaining tube 112 to allow the cap 120 to securely fit around the retaining tube 112 distal end. The cap 120 and the retaining tube 112 distal end can include mated threads to screw the cap 120 into place or the cap 120 can attach by snapping on the retaining tube 112. The cap 120 can be made of a liquid impervious material to prevent the passage of any fluids out of the retaining tube 112. The cap 120 can be reinforced using a sealing gasket 130.

A resizable chamber 124 is formed by the space between the cap 120 and the plunger base 118. The chamber 124 size can be selected or adapted by depressing the plunger base 118 to an appropriate distance from the cap 120. In an embodiment where the chamber 124 contains any of the bone materials 132 such as demineralized bone material, moldable material or formed bone compositions described herein, the plunger 116 can be depressed such that the plunger base 118 contacts the bone material 132. The chamber 124 can be resized by retracting the plunger 116 to accommodate for changes in the bone material 132 contained in the chamber 124. In various embodiments, a locking mechanism such as a notch or flap inside of the retaining tube wall can be included to maintain chamber 124 size where the plunger base 118 can not be retracted beyond the notch.

The side port 122 is located towards the distal end of the retaining tube 112. Preferably, the side port 122 is located in close proximity to the cap 120. The side port 122 is a valve which allows for the passage of a material into the chamber 124. The valve can be a bidirectional valve or a one-way valve. In various embodiments, the side port valve 122 can also allow for the passage of fluids out of the chamber. The side port valve 122 can also allow for the selective passage of solid materials. Any suitable syringe can be attached to the side port 122 to inject the hydration media into the chamber 124. Optionally, the bone material 132 can be placed inside of the chamber 124 through a retaining tube 112 opening. The side port 122 can include threads to mate with the connector 136, as detailed below.

Preferably, the chamber 124 contents, such as bone material 132, are under a vacuum. Air can be withdrawn from the chamber 124 using a vacuum syringe 134 at the side port 124 to create a partial vacuum in the cavity where the bone composition resides. The plunger base 118 and the cap 120 can be utilized to prevent disruption of the vacuum state.

Figure 3:
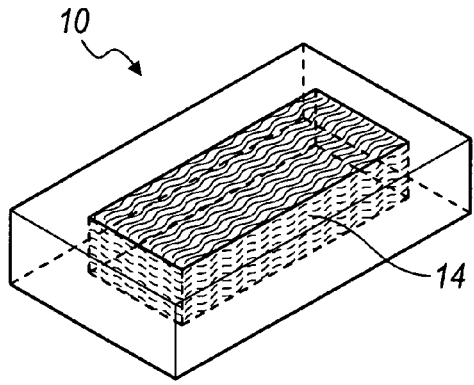
FIG. 3 depicts a formed bone composition having a bone forming composition in the channels according to various embodiments.
Figure 4:
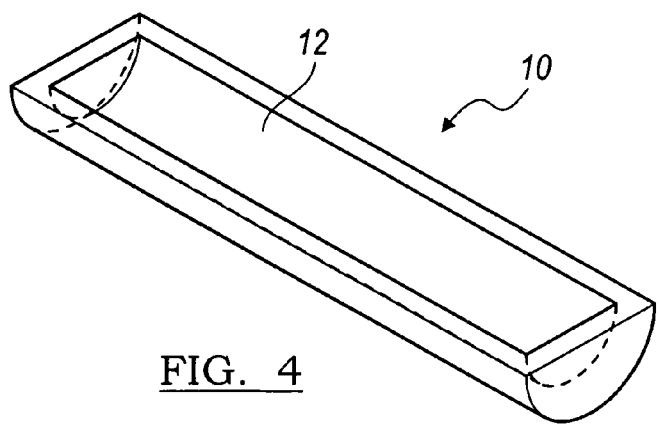
FIG. 4 depicts a curved formed bone composition having channels according to various embodiments.

In various embodiments, the chamber 124 and the cap 120 can be a single unit, as depicted in FIG. 3. The combined cap 120 and chamber 124 can provide various shapes of the formed composition. As depicted in FIG. 4 and for exemplary purposes only, the formed composition will be a disc.

Returning to FIGS. 1 and 2, the hydrating tube 114 comprises a distal end, a proximal end and a connector 136 for attachment to the side port valve 122. At the distal end, the connector 136 can include a syringe tip adapted to mate with the side port 122. The connector 136 can include threads which mate with two engaging threads on the side port 122, such that the hydrating tube 114 is screwed onto the retaining tube 112. At the proximal end, the hydrating tube 114 can be a closed surface or it can include a plunger 138, as depicted. The plunger 138 can be used to facilitate the uptake hydration media 140 or displacement of vacuum space inside of the chamber with the hydration media 140. In various embodiments, the hydrating tube 114 can also be a soft pouch or bag to contain the hydration media 140.

The hydration media 140 is preferably an aqueous solution including, but not limited to, saline, water or a balanced salt solution (e.g., 1140 ml NaCl, 5.4 ml KCl, pH 7.6). Various forms of aqueous hydration media 140 also include blood including, but not limited to, whole blood and blood components such as, red blood cells and components, white blood cells and components, plasma, plasma fractions, plasma serum, platelet concentrate, blood proteins, thrombin, and coagulation factors. As further detailed, later herein, a pressure differential draws the hydration media 140 into the chamber 124 of the retaining tube 112.

The hydration apparatus 110 can also include a vacuum syringe 134. The vacuum syringe 134 also has a connector 136 adapted to mate with the side port valve 122 of the retaining tube. The vacuum syringe 134 is adapted to remove moisture from the retaining tube 112.

Figure 10A:
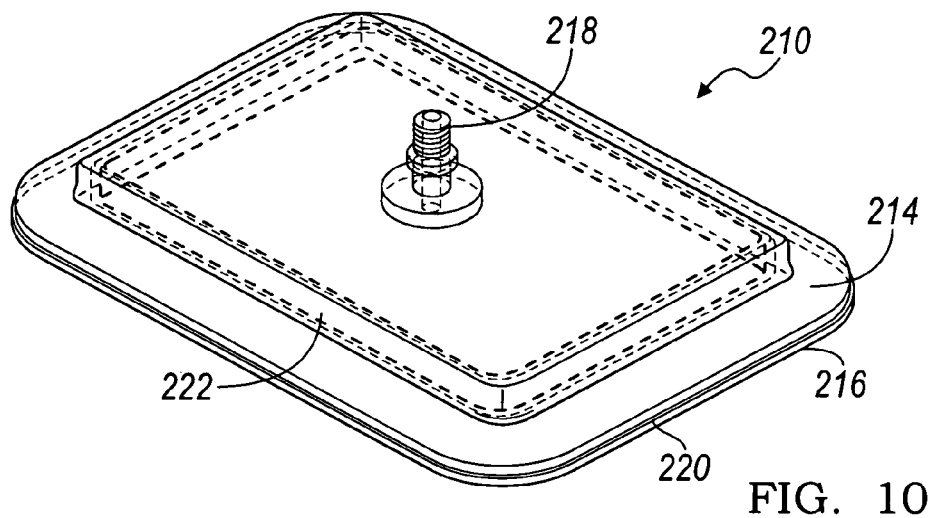
FIGS. 10A through 10C depict a sleeve type hydration apparatus according to various embodiments.

Referring to FIGS. 10A through 13, a hydration apparatus 210 is provided. The hydration apparatus 210 includes a sleeve 212. The sleeve 212 includes a proximal surface 214 and a distal surface 216. The sleeve 212 has dimensions which substantially conform to (or have a close fit with) the dimensions of the formed bone graft 222 contained therein. The substantial conformity or close fit is due to the combination of the dimensions of the sleeve and the vacuum pressure under which the formed bone graft 222 is maintained in the hydration apparatus 210. As shown in FIG. 10A, the sleeve 212 is generally rectangular in shape and fits within a close proximity of the outer diameter of the formed bone graft 222. Referring to FIG. 10B, the sleeve 212 is adapted to securely and closely house the formed bone composition such that the trough style bone composition and the channels 224 therein are contoured by the sleeve as indicated by creases 226 in the sleeve 212.

Figure 10B:
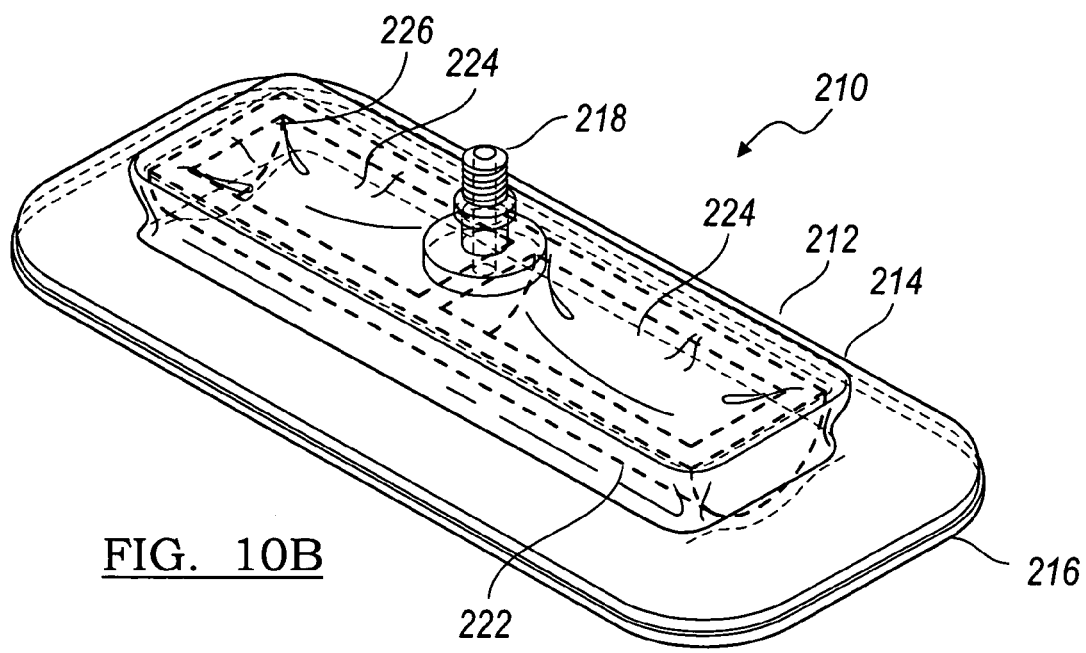
Figure 10C:
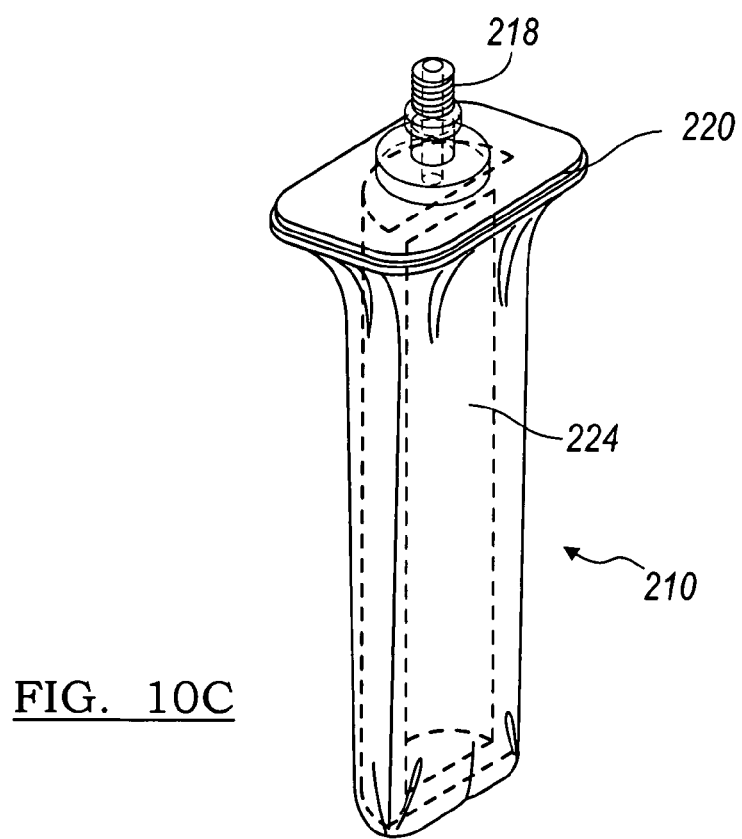
Figure 12:
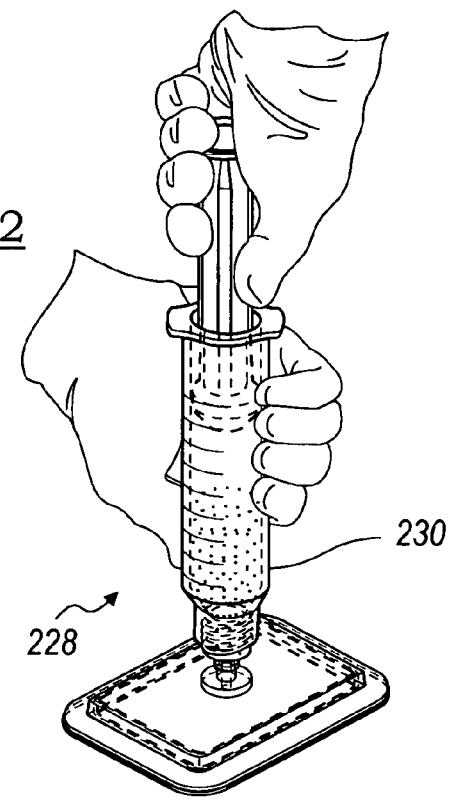
FIG. 12 depicts arranging a hydration media to hydrate the formed bone composition.

The sleeve 212 includes a port 218 having a valve. The valve can be a bidirectional valve or a one-way valve. Although not depicted, the sleeve 212 can include multiple ports 218. The port 218 can be located on the proximal surface 214, the distal surface 216, or any other area of the sleeve 212. As shown in FIG. 10C, the port 218 is located on the lid 220. The port 218 valve allows for the passage of fluids into of the sleeve 212. The port valve 218 can also allow for the selective passage of solid materials. Any suitable syringe can be attached to the port 218 to inject the hydration media 230 into the sleeve 212.

Figure 11:
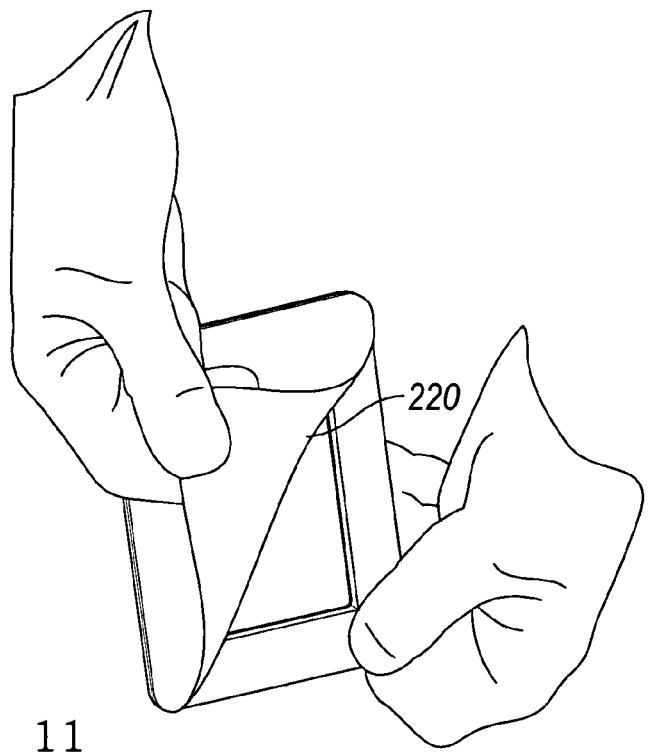
Figure 13:
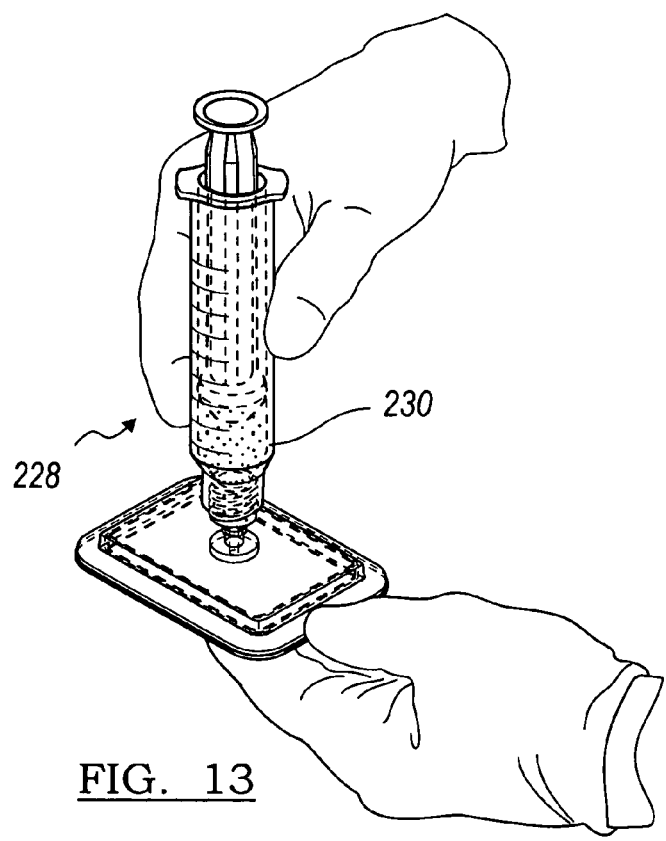
FIG. 13 depicts the hydration media advancing into the sleeve type hydration apparatus.

The sleeve 212 includes a lid 220. As depicted, the lid 220 is located at the distal surface 216 of the sleeve 212. The lid 220 assists in retaining the formed bone graft 222 in the hydration apparatus 210 and prevents unintentional misplacement of the formed bone graft 222 from the hydration apparatus. The lid 220 can be removable in that the lid snaps off of the distal surface of the hydration apparatus 210 or the lid 220 can be a peel-off style lid which is secured to the hydration apparatus using a semi-permanent adhesive. The lid 220 can be sized for easy manipulation by the hands of a user during hydration of the formed composition and during removal of the lid, as depicted in FIGS. 13 and 11, respectively.

The sleeve 212, lid 220, and other components of the hydration apparatus 210 can be made of any suitable material. The sleeve 212 is preferably durable, has barrier resistance to moisture, chemicals, grease, and bacteria, maintains its integrity upon exposure to low temperatures and is easy to handle in a medical or clinical setting. Regions of the sleeve 212 and the hydration apparatus 210 can also be flexible to allow for contouring against the formed bone composition 222. Suitable packaging materials can include thermoplastic films, polyester films, para-aramid fibers, polyethylene fibers, and combinations thereof. Moisture resistant foils can also be used to package the formed bone composition 222.

In various embodiments, the hydration apparatus 210 is a combination of various materials. For example, where a peel off lid 220 is used, it may be advantageous to have the lid materials be of a sufficient strength to prevent unintentional dislodging of the formed bone composition 224 from within the hydration apparatus, yet still be flexible enough for easy removal by a user.

To use the hydration apparatus 210, a syringe 228 is connected to the port 218. The syringe 228 and the port 218 can have mating threads which create a connection between the hydration apparatus 210 and the syringe 228. The formed bone composition 222 is contained in the hydration apparatus 210 under a partial or full vacuum. The pressure differential between the interior of the hydration apparatus 210 and the hydration media 230 within the syringe 228 causes the hydration media 230 to advance from the syringe 228 and into the interior of the hydration apparatus 210 to cause the dehydrated formed bone composition 222 to hydrate. Suitable hydration media include those listed above herein.

Kits

Kits according to various embodiments of the present teachings comprise:

(a) an apparatus for hydrating formed bone compositions; and (b) a hydration media.

The kits can contain a single apparatus 110 or 210 and the corresponding hydration media 140 or 228, respectively, or they can also include various combinations of the components in the same or different quantities. The kit can comprise several tubes of a single or different hydration media 140 or 228 in the same or different quantities.

The kits can also include various formed bone compositions. In various embodiments, the kit can comprise a plurality of apparatus 110 or 210 each having different shaped formed bone compositions such as a ring, a cylinder, block, or trough, for example, to provide formed bone compositions which can be individually or successively inserted into a site in need thereof. Instructions for use of the apparatus 110 or 210 and the hydration media 140 or 228 can also be included in the kit, such as a pamphlet, handbook, audio recording, or video.

Methods of Using Hydration Apparatus

Methods of using various apparatus according to embodiments of the present teachings comprise:

(a) providing a dehydrated formed bone composition under a vacuum in a container comprising a port;

(b) connecting a hydrating tube containing a hydration media to the port;

(c) drawing the fluid through the port and into the container to hydrate the formed bone composition.

In embodiments utilizing the hydration apparatus 110, the container housing the dehydrated formed bone composition is the retaining tube 112. The formed bone composition is contained in the retaining tube 112 in a vacuum or under partial vacuum conditions. The composition 132 can be dehydrated before addition to the chamber or can be dehydrated while in the chamber 124 via the side port 122, as described above. The hydrating tube 114 containing the hydration media 140 is connected to the side port 122. The hydrating tube 114 can also include a gas space to facilitate passage of the liquid into the chamber 124. The formed bone composition 132 and the pores therein are under at least partial vacuum conditions. The combined vacuum conditions within the apparatus 110 and within the pores aids in drawing the hydration media 140 liquid into the pores and thereby use of the system achieves near complete hydration in minutes. Depending upon the size of the formed composition 132 and the relative viscosity of the hydration media 140, hydration time can range between one and ten minutes. The fixed amount of vacuum space in the chamber 124 prevents the excessive uptake of hydration media 140. After hydration, the cap 120 on the apparatus 110 can be unscrewed and the user can engage the plunger 116 to eject the hydrated graft from the chamber 124, as depicted in FIG. 5. The hydrated composition can be placed directly into the defect site at the surgery or can be placed into a holding dish prior to use in a bone site, as depicted.

In embodiments utilizing the hydration apparatus 210, the container housing the dehydrated formed bone composition is the sleeve 212. Similar to the description for the hydration apparatus 210, the vacuum conditions within the apparatus 210 and within the pores aid in drawing the hydration media 230 into the pores and the system achieves near complete hydration in minutes. The lid 220 can be peeled away from the sleeve 212 or snapped off of the sleeve 212. The hydrated composition can be placed directly into the defect site at the surgery.

In various embodiments using the trough-style formed compositions 222, a bone building material contained in the channel(s) 224 can be simultaneously hydrated with the formed bone composition 222. In other embodiments using the trough-style formed composition 222, the bone building material can be placed in the channel(s) 224 after the formed composition 222 is hydrated and removed from the sleeve 212.

EXAMPLES

Example 1

Cancellous bone is harvested and adherent tissue are removed. The bone is milled into particles of 1500 microns and 810 microns. The bone is soaked in a solution of 100% ethanol, volume to volume, in deionized/distilled water to remove fat and kill microorganisms. The larger (1500 microns) bone particles are set aside. The smaller (810 microns) bone particles are placed in a 0.5 N hydrochloric acid bath and soaked overnight. The calcium ion concentration of the bone particles is monitored by measuring the ion concentration of the acid solution with a calcium specific electrode. The calcium concentration reaches 1% and the bone is removed from the acid bath. The de-calcified bone is washed with deionized/distilled water until the runoff rinse solution reaches a neutral pH level. To prepare a bone repairing composition, 25 grams of the demineralized bone (1% calcium, 810 microns) is mixed with 100 grams of a saline solution. The mixture is autoclaved at 121° C. under a pressure of 15 psi for 60 minutes to form the gel carrier. The carrier is mixed with 28 grams of demineralized bone (1% calcium, 810 microns) and a paste is formed. Additionally, 2.8 grams of the reserved natural bone chips (1500 microns) are added to the paste. The paste is spread into a square shaped mold using a spatula. The mold and paste are placed inside of a sterilized Tyvek®Mylar® dual chamber package. Moisture is withdrawn from the package by lyophilization and removed until the moisture content in the paste is less than about 6% of the cast weight. The freeze dried formed bone composition is a square patch measuring 4 cm×4 cm and having a thickness of 0.3 cm.

Example 2

A bone repairing composition is prepared according to the method described in Example 1. The carrier comprises 100 grams of saline and 20 grams of demineralized bone. The paste is formed by adding 30 grams of bone material to the carrier. The paste is placed into a tubular shaped mold which is lined with platelet concentrate to coat outer surfaces of the composition. The final dried composition is a cylinder having a diameter of 1.25 cm and a base height of 2.5 cm.

Example 3

A bone repairing composition is prepared according to the method of Example 1. The carrier comprises 100 grams of saline and 15 grams of demineralized bone. The paste is formed by adding 32.85 g of bone material to the carrier. Additionally, 3.285 grams of reserved natural bone chips are added. The composition is formed into a rectangular patch, and lyophilized. The pre-lyophilization mixture has the following weight percentages: 9.92% of the carrier, 21.74% of the bone material component, 66.17% water and 2.17% natural bone chips. After lyophilization, the final formed composition has the following weight percentages: 29.33% carrier component, 64.24% bone material component and 6.41% natural bone chips.

Example 4

A patch for use in craniofacial surgery is prepared according to the method of Example 1. The carrier component comprises 100 grams of saline and 25 grams of demineralized bone. The paste is formed by adding 35.714 g of demineralized bone to the carrier. Additionally, 3.57 grams of natural bone chips are added. The patch has the following weight percentages: 38.89% carrier component, 55.56% bone material component and 5.55% natural bone chips. The patch is a circle having a diameter of 9.5 cm and a thickness of 0.5 cm. The patch is hydrated while in the injury site using the subject's blood as the source of water.

The patch is heated using the LactoSorb® Heat Pack (Biomet, Inc.; Warsaw, Ind., USA) for 1minute prior to application into the injury site. The patch is malleable thereby facilitating anatomical contouring into the injury site. The patch is hydrated while in the injury site using the subject's blood as the source of water.

Example 5

Spinal surgery fusion is enhanced by using a combination of patch and cylindrical shaped formed compositions according to Examples 1 and 2. In this example, the formed compositions are coated with calcium triphosphate and Bone Morphogenic Protein-2 prior to implantation.

Example 6

Posterolateral fusion is enhanced by using a trough-style formed bone composition having two channels made according to the methods and formulations of Examples 1 and 2. The first channel in the trough-style formed bone composition is filled with autograft bone chips and the second channel is filled with a mixture of Bone Morphogenic Protein-2, rifampin, and minocycline.

Example 7

An x-ray is taken of a subject's fractured hip. The x-ray dimensions are scaled to match the subject's height/size and a site specific cast composition according to Example 1 is prepared. The composition is implanted at the site of the fracture.

Example 8

A kit is provided containing an apparatus and a formed bone composition according to the formula in Example 4. The apparatus (depicted in FIG. 2) includes a retaining tube having a side port and a hydrating tube containing a hydration media which is adapted to connect with the side port. The dried formed bone composition is lodged in a cylindrical chamber formed between a plunger disposed in the retaining tube and a capped end on the tube. The hydrating tube is connected with the side port valve. Vacuum pressure within the pores of the formed bone composition draws hydration media from the hydrating tube into the pores of the dehydrated formed composition. After five minutes, the formed composition is hydrated and ready for implantation.

Example 9

The kit as described in Example 8 includes four tubes of hydration media comprising one platelet concentrate solution, two saline solutions and one plasma serum solution. The hydrating tube is connected to the side port and the media is transferred into the chamber. The process is repeated with each of the four tubes of hydration media until the formed composition is completely hydrated. Instructions for using the kit and optimizing the order of hydration media addition are also provided.

What is claimed is:

1. A rigid formed composition for application to a bone surface of a human or animal subject, the rigid formed composition being made by drying a paste composition prior to application to the subject, the paste consisting of:
   (a) a first component that is a bone material selected from the group consisting of bone powder, bone chips, bone shavings, and mixtures thereof; and
   (b) a second component that is a carrier, wherein the carrier is denatured demineralized bone material; wherein the composition is formed into a rigid shape suitable for administration to the bone, wherein the shape is selected from a sheet, a patch, a block, a ring, a disc, a cylinder, or a shape for a specific site.

2. The formed composition according to claim 1, wherein the first component bone material is demineralized bone powder.

3. The formed composition according to claim 2, wherein the first component bone material has a particle size of less than 1000 microns.

4. The formed composition according to claim 3, wherein the first component bone material has a particle size of less than 850 microns.

5. A rigid formed composition for application to a bone surface of a human or animal subject the rigid formed composition being made by drying a paste composition prior to application to the subject, the paste consisting of:
   (a) a first component that is a bone material that is a mixture of bone powder and bone chips; and
   (b) a second component that is a carrier, wherein the carrier is denatured demineralized bone material; wherein the composition is formed into a rigid share suitable for administration to the bone, wherein the shape is selected from a sheet, a patch, a block, a ring, a disc, a cylinder, or a shape for a specific site.

6. The formed composition according to claim 5, wherein the large dimension of the demineralized bone chips is from about 750 to about 2000 microns.

7. The formed composition according to claim 6, wherein the large dimension is from about 750 to about 1500 microns.

8. The formed composition according to claim 1, wherein from about 10% to about 40% of the composition is first component bone material.

9. The formed composition according to claim 8, wherein from about 20% to about 30% of the composition is first component bone material.

10. The formed composition according to claim 1, wherein the carrier is made of denatured demineralized bone in an amount of from about 0.2% to about 40% by weight of carrier.

11. The formed composition according to claim 10, wherein the carrier is made of denatured demineralized bone in an amount of from about 0.5% to about 25% by weight of carrier.

12. The formed composition according to claim 1, wherein the carrier is made of denatured demineralized bone in an amount of from about 10% to about 20% by weight of carrier.

13. The formed composition according to claim 1, wherein the carrier is made by a process comprising:
    (a) mixing demineralized bone powder with water; and
    (b) heating the mixture of the powder and water under pressure.

14. The formed composition according to claim 13, wherein the heating is autoclaving the mixture.

15. A rigid formed composition for application to a bone surface of a human or animal subject the rigid formed composition being made by drying a paste composition prior to application to the subject, the paste consisting of:
    (a) a first component that is a bone material selected from the group consisting of bone powder, bone chips, bone shavings, and mixtures thereof;
    (b) a second component that is a carrier, wherein the carrier is denatured demineralized bone material; wherein the composition is formed into a rigid share suitable for administration to the bone, wherein the shape is selected from a sheet, a patch, a block, a ring, a disc, a cylinder, or a shape for a specific site; and
    (c) a third component that is a bone building material.

16. The formed composition according to claim 15, wherein the bone building material is selected from the group consisting of: calcium-containing ceramic materials, nutrient factors, bone morphogenic proteins, growth factors, antimicrobials, anti-inflammatory agents, blood products, and mixtures thereof.

17. The formed composition according to claim 16, wherein the bone building material is a calcium-containing ceramic material.

18. The formed composition according to claim 16, wherein the bone building material is a bone morphogenic protein, a growth factor, or mixtures thereof.

19. The formed composition according to claim 16, wherein the bone building material is a blood product.

20. The formed composition according to claim 1, wherein the shape is a patch.

21. The formed composition according to claim 1, wherein the bone material and the denatured demineralized bone are autologous with the subject.

22. A method for making a rigid formed composition for application to a bone surface of a human or animal subject, the composition being made rigid by drying prior to application to the subject, the method consisting of:
    (a) mixing a demineralized bone material and water;
    (b) heating the mixture of demineralized bone material and water to form a carrier and to denature the demineralized bone;
    (c) mixing the carrier with a second bone material to form a moldable composition, wherein the second bone material is selected from the group consisting of: bone powder, bone chips, bone shavings, and mixtures thereof;
    (d) molding the moldable composition to produce a formed composition having a shape suitable for administration to the bone; and
    (e) drying the formed composition to provide the rigid formed composition.

23. The method according to claim 22, wherein the second bone material is demineralized bone powder.

24. The method according to claim 23, wherein the demineralized bone powder has a particle size of less than about 850 microns.

25. A method according to claim 22, wherein the second bone material consists of demineralized bone powder and demineralized bone chips.

26. The method according to claim 22, wherein from about 20% to about 30% of the rigid formed composition is the second bone material.

27. The method according to claim 22, wherein the carrier is from about 10% to about 20% by weight of denatured demineralized bone.

28. A method for making a rigid formed composition for application to a bone surface of a human or animal subject, the composition being made rigid by driving prior to application to the subject, the method consisting of:
    (a) mixing a demineralized bone material and water;
    (b) heating the mixture of demineralized bone material and water to form a carrier and to denature the demineralized bone;
    (c) mixing the carrier with a second bone material, wherein the second bone material is selected from the group consisting of: bone powder, bone chips, bone shavings and mixtures thereof, and a third component that is a bone building material to form a moldable composition;
    (d) molding the moldable composition to produce a formed composition having a shape suitable for administration to the bone; and
    (e) drying the formed composition to provide the rigid formed composition.

29. The method according to claim 28, wherein the bone building material is a calcium-containing ceramic material.

30. The method according to claim 28, wherein the bone building material is a bone morphogenic protein, a growth factor, or mixtures thereof.

31. The method according to claim 22, wherein the rigid formed composition has a shape that is a patch, a block, or a shape for a specific site.

32. The method according to claim 22, wherein the second bone material and the demineralized bone are from a single donor.

33. The method according to claim 32, wherein the donor is the subject.

34. The method according to claim 22, wherein the heating is autoclaving the mixture.

35. The method according to claim 34, wherein the autoclaving is conducted at a temperature of from about 100° C. to about 150° C., and at a pressure of from about 10 psi to about 20 psi, for from about 60 mm to about 2 hours.

36. The method according to claim 22, wherein the drying technique is selected from the group consisting of lyophilizing, vacuum drying, air drying, temperature flux drying, and molecular sieve drying.

37. The method according to claim 36, wherein the drying technique is lyophilizing.

38. A method for making a rigid formed composition for application to a bone surface of a human or animal subject, the composition being made rigid by drying prior to application to the subject, the method consisting of:
(a) mixing a demineralized bone material and water;
(b) heating the mixture of demineralized bone material and water to form a carrier and to denature the demineralized bone;
(c) mixing the carrier with a second bone material to form a moldable composition, wherein the second bone material is selected from the group consisting of: bone powder, bone chips, and mixtures thereof;
(d) molding the moldable composition to produce a formed composition having a shape suitable for administration to the bone;
(e) driving the formed composition to provide the rigid formed composition by lyophilization; and
(f) packaging the composition after lyophilizing in a substantially air-impermeable package.

39. The method according to claim 38, wherein the package is made of a material selected from the group consisting of: thermoplastic films, polyester films, para-aramid fibers, polyethylene fibers, and combinations thereof.

40. A rigid formed composition for application to a bone surface of a human or animal subject made by the method of claim 22.

41. The rigid formed composition of claim 40, wherein the moldable composition is dried using a drying technique selected from the group consisting of lyophilizing, vacuum drying, air drying, temperature flux drying, and molecular sieve drying.

42. The rigid formed composition of claim 41 wherein the composition is packaged after drying in a substantially air-impermeable package that is made of a material selected from the group consisting of: thermoplastic films, polyester films, para-aramid fibers, polyethylene fibers, and combinations thereof.

43. A rigid formed composition for application to a bone surface of a human or animal subject, the rigid formed composition being made by drying a paste composition prior to application to the subject, the paste consisting of:
(a) a first component that is a bone material selected from the group consisting of bone powder, bone chips, bone shavings, and mixtures thereof; and
(b) a second component that is a carrier, wherein the carrier is denatured demineralized bone material; wherein the composition is formed into a rigid trough shape suitable for administration to the bone, and wherein the trough has at least one channel.

44. The rigid formed composition according to claim 43, wherein the trough has two channels.

45. The rigid formed composition according to claim 43, wherein at least one channel contains a bone building material.

* * * * *

UNITED STATES PATENT AND TRADEMARK OFFICE
CERTIFICATE OF CORRECTION

| | | |
|---|---|---|
| PATENT NO. | : 7,670,384 B2 | Page 1 of 1 |
| APPLICATION NO. | : 11/407409 | |
| DATED | : March 2, 2010 | |
| INVENTOR(S) | : Mukesh Kumar et al. | |

It is certified that error appears in the above-identified patent and that said Letters Patent is hereby corrected as shown below:

Col. 18, line 67 (claim 5): "share" should be -- shape --

Col. 19, line 42 (claim 15): "share" should be -- shape --

Col. 20, line 32 (claim 28): "driving" should be -- drying --

Col. 20, line 67 (claim 35): "mm" should be -- min --

Col. 21, line 22 (claim 38): "driving" should be -- drying --

Signed and Sealed this

Fifteenth Day of June, 2010

David J. Kappos
*Director of the United States Patent and Trademark Office*